United States Patent
Kim et al.

(10) Patent No.: US 7,202,360 B2
(45) Date of Patent: Apr. 10, 2007

(54) METHOD FOR PREPARING RISPERIDONE

(75) Inventors: Nam-Du Kim, Osan-si (KR); Jae-Heon Lee, Yongin-si (KR); Moon-Sub Lee, Daejeon (KR); Young-Kil Chang, Seoul (KR); Gwan-Sun Lee, Seoul (KR)

(73) Assignee: Hanmi Pharm Co., Ltd., Kyungki-do (KR)

( * ) Notice: Subject to any disclaimer, the term of this patent is extended or adjusted under 35 U.S.C. 154(b) by 43 days.

(21) Appl. No.: 10/531,299

(22) PCT Filed: Oct. 17, 2003

(86) PCT No.: PCT/KR03/02171

§ 371 (c)(1),
(2), (4) Date: Apr. 14, 2005

(87) PCT Pub. No.: WO2004/035573

PCT Pub. Date: Apr. 29, 2004

(65) Prior Publication Data

US 2006/0004024 A1 Jan. 5, 2006

(30) Foreign Application Priority Data

Oct. 18, 2002 (KR) .................... 10-2002-0063696

(51) Int. Cl.
*C07D 239/70* (2006.01)
*A01N 43/90* (2006.01)
*A61K 31/519* (2006.01)
*C07D 211/18* (2006.01)

(52) U.S. Cl. .................... 544/282; 514/259.1; 546/232

(58) Field of Classification Search ................ 544/282
See application file for complete search history.

(56) References Cited

U.S. PATENT DOCUMENTS

| 4,485,107 A | 11/1984 | Kennis et al. |
| 4,804,663 A | 2/1989 | Kennis et al. |

FOREIGN PATENT DOCUMENTS

| EP | 0196132 A2 | 10/1986 |
| ES | 2050069 A1 | 5/1994 |
| ES | 2 074 966 | 9/1995 |
| KR | 1996-0009435 B1 | 1/1999 |
| WO | WO 0185731 A1 | 5/2000 |
| WO | WO 0212200 A1 | 2/2002 |
| WO | WO 03/042242 | * 5/2003 |

* cited by examiner

*Primary Examiner*—Deepak Rao
*Assistant Examiner*—Cecilia Jaisle
(74) *Attorney, Agent, or Firm*—Sughrue Mion, PLLC

(57) ABSTRACT

Risperidone is prepared in a high yield by reacting 2,4-difluorophenyl(4-piperidinyl)methanone oxime hydrochloride and 3-(2-chloroethyl)-6,7,8,9-tetrahydro-2-methyl-4H-pyrido[1,2-a]pyrimidin-4-one in an aqueous alkali hydroxide solution having an alkali hydroxide concentration in the range of 20 to 40%.

6 Claims, 1 Drawing Sheet

METHOD FOR PREPARING RISPERIDONE

FIELD OF THE INVENTION

The present invention relates to an improved method for preparing risperidone.

BACKGROUND OF THE INVENTION

Risperidone, which is the generic name for the compound of formula (I), 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one, is a potent antipsychotic agent, especially useful for treating schizophrenia:

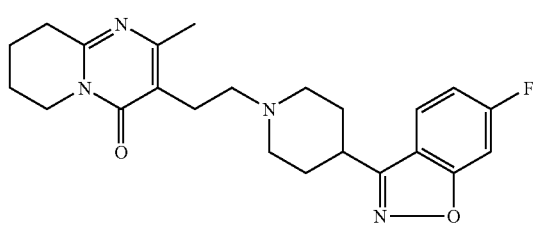

There have been reported a number of methods for risperidone synthesis but these methods generally suffer from the problems of low yield and complicated procedures.

For example, the benzisoxazol derivative of formula (E) obtained by ring closure of the oxime derivative of formula (II) is coupled with the pyrimidine derivative of formula (IV) to give risperidone, as shown in Scheme 1.

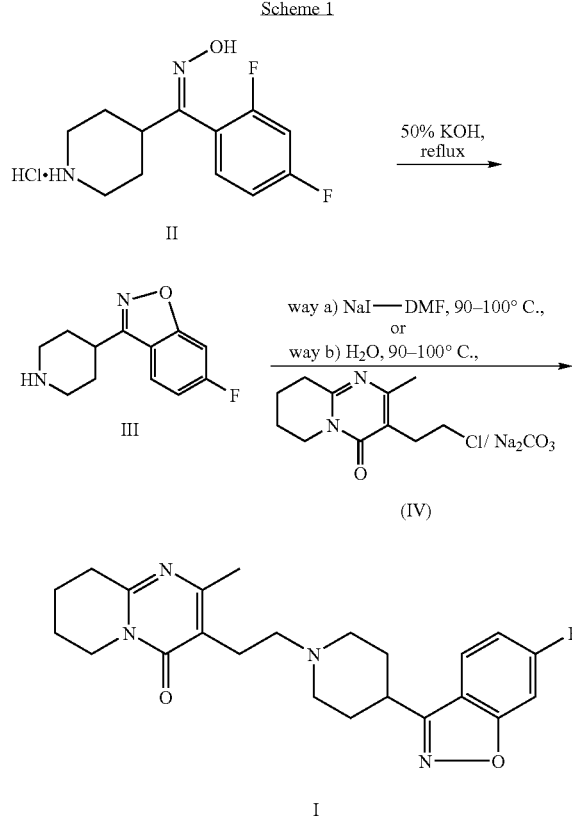

In Scheme 1, the coupling reaction of the benzisoxazol derivative (III) and the pyrimidine derivative (IV) may be performed by the method disclosed in U.S. Pat. No. 4,804,663, wherein the coupling reaction is performed in N,N-dimethylformamide in the presence of a sodium iodide catalyst (way a). However, this method gives a low yield of about 46% (overall yield of about 35%) due to the occurrence of side reactions such as self-polymerization of the benzisoxazol derivative (III).

Alternatively, the coupling reaction may be carried out using the method, International Publication No. WO 01/85731 which uses water as solvent instead of N,N-dimethylformamide so as to suppress the side reactions (way b). However, this method also gives an overall yield of only 55%.

Korean Patent Publication No. 96-9435, on the other hand, discloses a method as illustrated in Scheme 2, wherein the compound of formula (V) obtained by coupling of the oxime derivative of formula (II) with the pyrimidine derivative of formula (IV) is subjected to ring closure in the presence of a strong base such as sodium hydride.

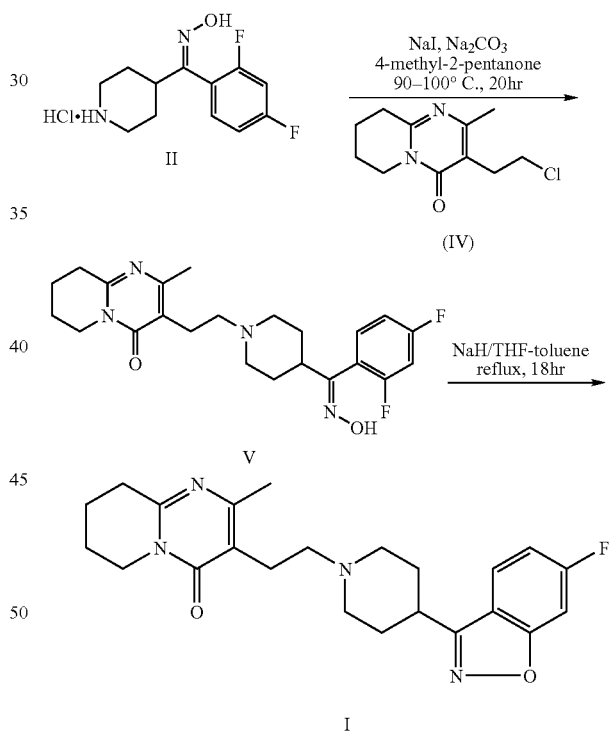

However, this method still has a problem in that the overall yield is only 45%. In addition, this method has to deal with the risk of sodium hydride explosion.

Further, Spanish Patent No. 2,050,069 discloses a method for preparing risperidone which is described in Scheme 3: the compound of formula (VII) obtained by coupling of the benzoylpiperidine derivative of formula (VI) and the pyrimidine derivative of formula (IV) is subjected to oximation to give the compound (V), and ring closure thereof gives risperidone.

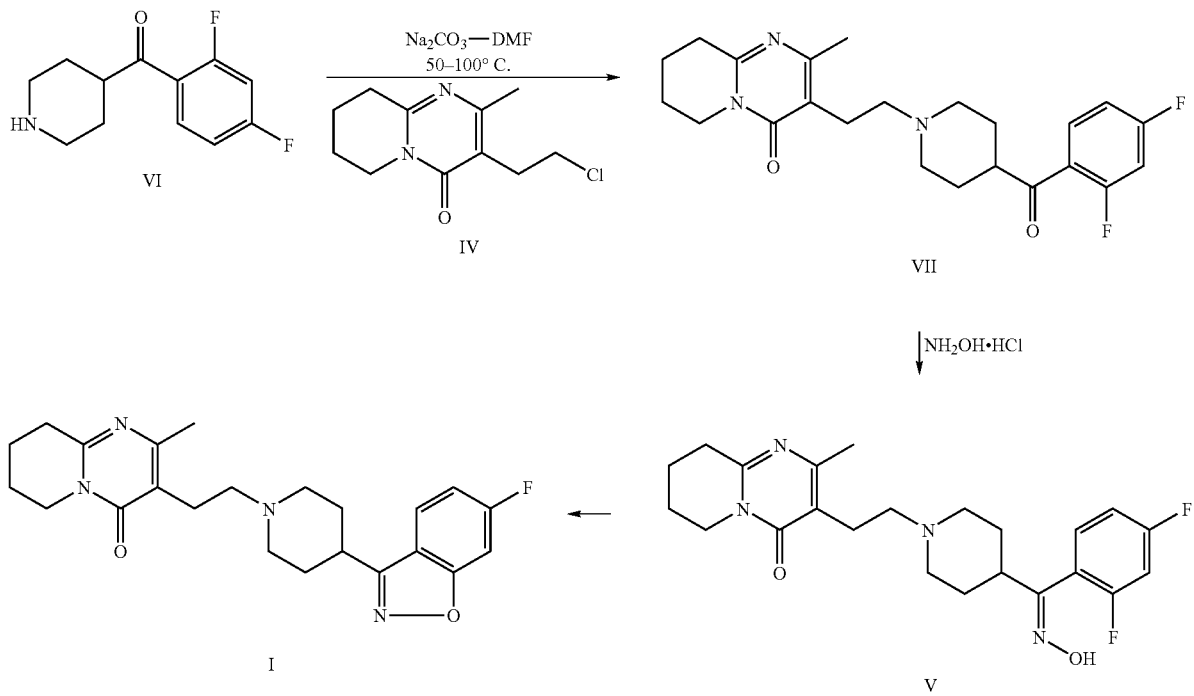

Scheme 3

This method also gives a low coupling yield of 63%, and complicated work-up procedures are required.

Spanish Patent No. 2,074,966 describes a method of preparing risperidone as presented in Scheme 4, wherein the risperidone of formula (I) is obtained by the reaction of the oxazol derivative of formula (IX) and the aminopyridin derivative of formula (VIII).

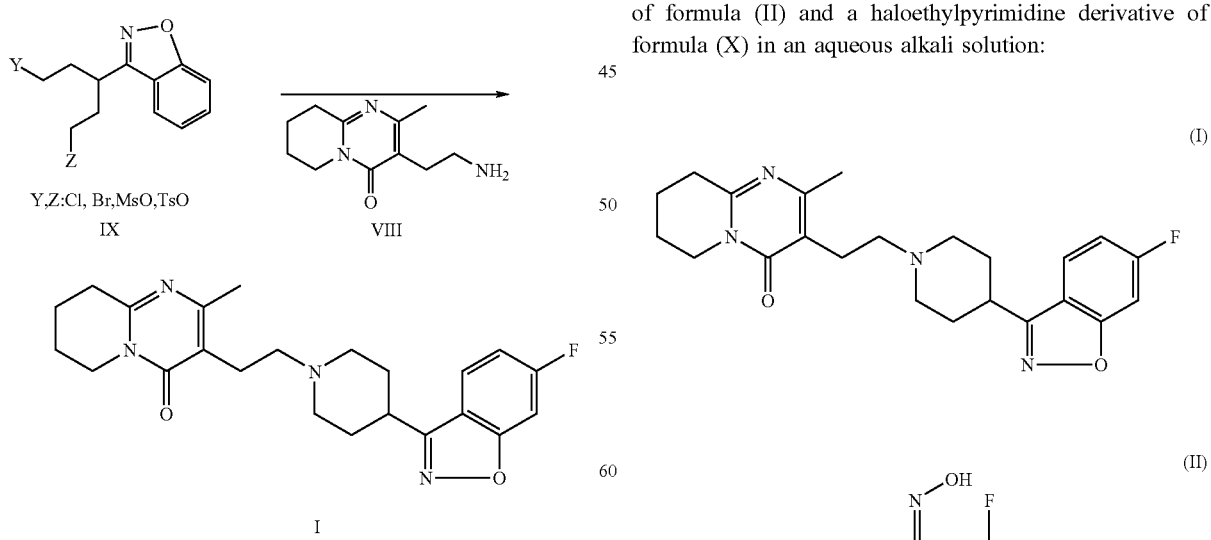

Scheme 4

However, this method is hampered by the problem that the processes of preparing the starting materials of formula (VIII) and (IX) are complicated.

SUMMARY OF THE INVENTION

Accordingly, it is an object of the present invention to provide a simple, improved method of preparing risperidone in a high yield.

In accordance with one aspect of the present invention, there is provided a method of preparing risperidone of formula (I) which comprises reacting the oxime derivative of formula (II) and a haloethylpyrimidine derivative of formula (X) in an aqueous alkali solution:

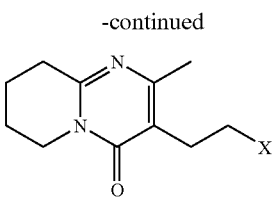

(X)

wherein, X is a halogen.

BRIEF DESCRIPTION OF THE DRAWINGS

The above and other objects and features of the present invention will become apparent from the following description of the invention, when taken in conjunction with the accompanying drawing, in which.

DETAILED DESCRIPTION OF THE INVENTION

Figure 1:
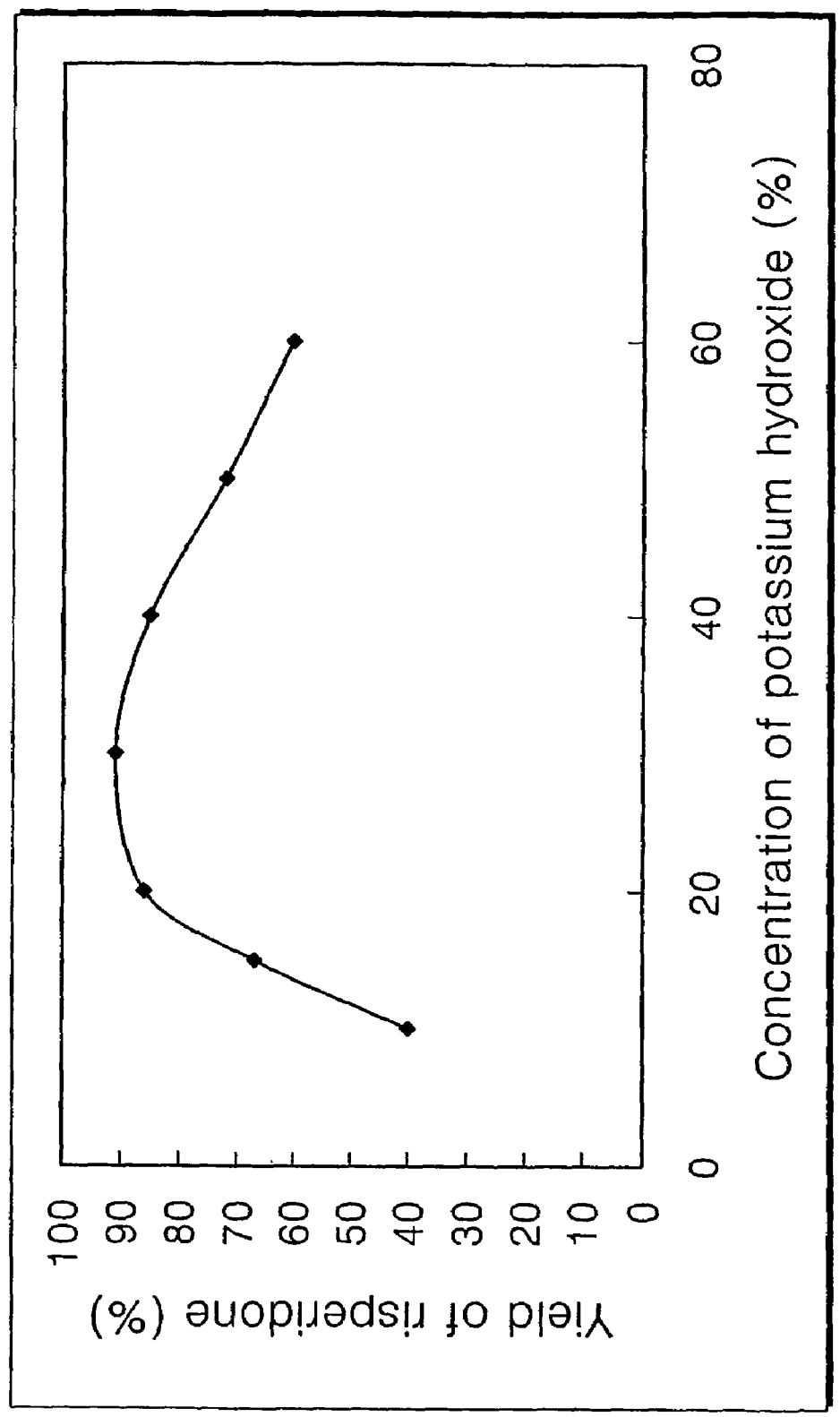
FIG. 1 shows the change in the yield of risperidone (%) with the concentration of potassium hydroxide (%), as observed in Reference Example.

The present invention is characterized by accomplishing the coupling reaction and the ring closure reaction in one step by way of using selected reactants in an aqueous alkali solution having an alkali hydroxide concentration in the range of 20 to 40%.

According to the present invention, the oxime derivative of formula (II), 2,4-difluorophenyl (4-piperidinyl) methanone oxime hydrochloride, and the haloethylpyrimidine derivative of formula (X), 3-(2-haloethyl)-6,7,8,9-tetrahydro-2-methyl-4H-pyrido[1,2-a]pyrimidin-4-one, are used as starting materials, which are commercially available or may be prepared in accordance with the methods described in U.S. Pat. Nos. 4,485,107 and 4,804,663.

In a preferred embodiment, the haloethylpyrimidine derivative of formula (X) may be employed in an amount ranging from 1.0 to 2.0 equivalents, preferably 1.1 to 1.3 equivalents, based on the amount of the oxime derivative of formula (II).

In a preferred embodiment, the concentration of alkali hydroxide in the aqueous alkali solution used in the present invention is in the range of 20 to 40% (w/v), preferably 30% (w/v). If the concentration of the alkali hydroxide is less than 20% (w/v), the yield decreases due to the generation of excessive by-products. On the other hand, if the concentration of the alkali hydroxide is more than 40% (w/v), the yield is decreased due to the increase of decomposed products.

Representative examples of the alkali hydroxide include sodium hydroxide, potassium hydroxide, lithium hydroxide and a mixture thereof, more preferably potassium hydroxide.

In a preferred embodiment, the aqueous alkali solution may be employed in an amount ranging from 5 to 15 ml, preferably 7 to 11 ml based on 1 g of the oxime derivative of formula (II).

In a preferred embodiment, the inventive reaction may be conducted at a temperature in the range of 100 to 140° C., preferably 100 to 130° C. for 1 to 6 hours, preferably, 1.5 to 3 hours.

In accordance with the present invention, risperidone can be obtained in a much higher yield of at least 80% than previously possible. Further, according to the present invention, the conventional coupling and the ring closure reactions, which comprise several cumbersome steps can be performed simultaneously in one step. In addition, risperidone obtained in the present invention may be refined to a purity of 99.5% or more, by a simple recrystallization procedure.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

PREPARATION EXAMPLE 1

Preparation of 2,4-difluorophenyl(4-piperidinyl)methanone oxime hydrochloride (the compound of formula II)

A) Preparation of 1-acetyl-4-(2,4-difluorobenzoyl)piperidine 67 g of 1,3-difluorobenzene and 133 g of ammonium chloride were added to 150 ml of dichloromethane, and then the mixture was cooled to room temperature. 98 g of 1-acetyl-4-piperidinecarbonyl chloride in 50 ml of dichloromethane was added thereto dropwise, and then the mixture was stirred at an elevated temperature for 3 hours. The reaction mixture was poured to a mixture of ice and hydrochloric acid, and the resulting mixture was extracted with 200 ml of dichloromethane. The organic phase was separated, dried over anhydrous magnesium sulfate, filtered, and the solvent was removed from the filtrate to obtain 55.9 g of the title compound (yield: 41%).

B) Preparation of 2,4-difluorophenyl(4-piperidinyl)methanone hydrochloride 56 g of 1-acetyl-4-(2,4-difluorobenzoyl)piperidine obtained in step A) was added to 190 ml of 6N hydrochloric acid, and then, the resulting mixture was refluxed for 5 hours. The reaction mixture was concentrated under a reduced pressure, 200 ml of 2-propanol was added to the residue, and then the mixture was stirred. The resulting solid was filtered and dried to obtain 46.6 g of the title compound (yield: 85%).

C) Preparation of 2,4-difluorophenyl(4-piperidinyl)methanone oxime hydrochloride 30 g of 2,4-difluorophenyl(4-piperidinyl)methanone hydrochloride obtained in step B) and 30 g of hydroxylamine hydrochloride were added to 50 ml of ethanol. 29.5 ml of N,N-dimethylethanolamine was added thereto dropwise while stirring at room temperature, and then the mixture was refluxed for 3 hours. The reaction mixture was cooled to room temperature, and the precipitated solid was filtered and dried to obtain 26.4 g of the title compound as a white crystal (yield: 96%).

PREPARATION EXAMPLE 2

Preparation of 3-(2-chloroethyl)-6,7,8,9-tetrahydro-2-methyl-4H-pyrido[1,2-a]pyrimidin-4-one (compound of formula X)

A) Preparation of 3-(2-chloroethyl)-2-methyl-4H-pyrido[1,2-a]pyrimidin-4-one 40 g of 2-aminopyridine and 75 ml of 3-acetyl-4,5-dihydro-2(3H)-furanone were added to 1.0 L of toluene, and then 200 ml of phosphorus oxychloride was added thereto dropwise over 1 hour. The resulting mixture was slowly heated and refluxed for 5 hours. The reaction mixture was concentrated under a reduced pressure and the residue was poured to a mixture of ice and ammonia water. The resulting solid was extracted with 1.0L of dichloromethane, dried and filtered. The filtrate was concentrated under a reduced pressure to remove dichloromethane and 500 ml of isopropanol was added to the residue. The resulting crystal was filtered, washed and dried to obtain 48.1 g of the title compound as a off-white crystal (yield: 52%).

B) Preparation of 3-(2-chloroethyl)-6,7,8,9-tetrahydro-2-methyl-4H-pyrido[1,2-a]pyrimidin-4-one 28 g of 3-(2-chloroethyl)-2-methyl-4H-pyrido[1,2-a]pyrimidin-4-one obtained in step A) was dissolved in 90 ml of 6N hydrochloric acid, 2.8 g of 10%-palladium was added thereto, and then the mixture was hydrogenated under a hydrogen pressure of 35 psi at room temperature for 8 hours. The reaction mixture was filtered through Cellite and the filtrate was concentrated under a reduced pressure, 200 ml of isopropanol was added to the residue, and then the mixture was stirred. The solid was filtered and dried to obtain 25.1 g of the title compound as a white crystal (yield: 90%).

EXAMPLE 1

Preparation of 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one (risperidone)

2.77 g of 2,4-difluorophenyl(4-piperidinyl)methanone oxime hydrochloride obtained in Preparation Example 1 and 2.26 g of 3-(2-chloroethyl)-6,7,8,9-tetrahydro-2-methyl-4H-pyrido[1,2-a]pyrimidin-4-one obtained in Preparation Example 2 were added to 27 ml of 30% aqueous potassium hydroxide, and then the resulting mixture was stirred at 120 to 130° C. for 90 minutes. The reaction mixture was cooled to room temperature, filtered, and the obtained solid was added to 16 ml of N,N-dimethylformamide. The resulting suspension was heated to 80° C., left at that temperature for 5 minutes, and then slowly cooled to room temperature. The resulting crystal was filtered, washed with 5 ml of water and dried to obtain 3.39 g of the title compound as a white crystal (yield: 82%).

Melting point: 167~169° C.;

Purity: 99.7% (by HPLC);

$^1$H-NMR (300 MHz, CDCl$_3$): δ 7.65–7.61 (m, 1H), 7.18–7.14 (m, 1H), 7.00–6.94 (m, 1H), 3.87–3.83 (m, 2H), 3.12–3.07 (m, 2H), 2.97–3.02 (m, 1H), 2.81–2.76 (m, 2H), 2.71–2.66 (m, 2H), 2.48–2.43 (m, 2H), 2.23 (s, 3H), 2.34–2.19 (m, 2H), 2.05–2.01 (m, 4H), 1.87–1.79 (m, 4H).

EXAMPLE 2

Preparation of 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one (risperidone)

The procedure of Example 1 was repeated except that 40% aqueous potassium hydroxide was used to obtain 3.27 g of the title compound as a white crystal (yield: 80%).

Purity: 99.5% (by HPLC);

Melting point and $^1$H-NMR data were the same as in Example 1.

COMPARATIVE EXAMPLE

Preparation of Risperidone in Accordance with International Publication No. WO 01/85731

A) Preparation of 4-(6-fluoro-1,2-benzisoxazol-3-yl)-piperidine (the compound of formula III)

5.52 g of 2,4-difluorophenyl(4-piperidinyl)methanone oxime hydrochloride obtained in Preparation Example 1 was added to 25 ml of 50% potassium hydroxide, and then the mixture was refluxed for 4 hours. Subsequently, the reaction mixture was cooled to room temperature, extracted twice with 25 ml portions of toluene. The combined organic phase was dried over anhydrous magnesium sulfate, filtered, and the filtrate was concentrated under a reduced pressure. The resulting solid was recrystallized from 20 ml of ether, to obtain 3.29 g of the title compound (yield: 75%).

$^1$H-NMR (300 MHz, CDCl$_3$): δ 7.67–7.71 (m, 1H), 7.22–7.26 (m, 1H), 6.97–7.09 (m, 1H), 3.16–3.27 (m, 3H), 1.92–2.08 (m, 4H).

B) Preparation of Risperidone 2.27 g of 4-(6-fluoro-1,2-benzisoxazol-3-yl)-piperidine obtained in step A) and 2.26 g of 3-(2-chloroethyl)-6,7,8,9-tetrahydro-2-methyl-4H-pyrido[1,2-a]pyrimidin-4-one obtained in Preparation Example 2 were added to a solution of 2.25 g of Na$_2$CO$_3$ in 12 ml of water. The resulting mixture was stirred at 85 to 90° C. for 4 hours, cooled to room temperature, and filtered. The resulting solid was added to 16 ml of N,N-dimethylformamide. The resulting suspension was heated to 80° C., left at that temperature for 5 minutes, and then slowly cooled to room temperature. The crystal was filtered, washed with 5 ml of water and dried to obtain 3.02 g of the title compound as a white crystal (yield: 73%).

The Melting Point and $^1$H-NMR Data Were the Same as in Example 1.

REFERENCE EXAMPLE

Change of the Yield of Risperidone (%) Depending on the Concentration of Potassium Hydroxide (%)

The procedure of Example 1 was repeated using 10, 15, 20, 30, 40, 50 or 60% aqueous potassium hydroxide and the yield of risperidone (by HPLC) was examined. The results are shown in Table 1 and FIG. 1.

TABLE 1

| Concentration of potassium hydroxide (%) | 10 | 15 | 20 | 30 | 40 | 50 | 60 |
|---|---|---|---|---|---|---|---|
| Yield of risperidone (%) | 40 | 67 | 86 | 91 | 85 | 72 | 60 |

As shown in Table 1 and FIG. 1, the yield of risperidone varies with the concentration of potassium hydroxide. The use of a potassium hydroxide concentration in the range of 20 to 40% provides risperidone at a good yield of at least 80%.

For reference, the comparison of the yields of risperidone according to the present invention and prior arts methods are shown in Table 2, for the purpose of verification of the effects of the present invention.

TABLE 2

| | Yield (%) | | |
|---|---|---|---|
| | Coupling reaction | Ring closure reaction | Overall reaction |
| U.S. Pat. No. 4,804,663 | 46 | 76 | 35 |
| International Publication No. WO 01/85731 | 72 | 76 | 55 |
| Korean Patent No. 96-9435 | 77 | 58 | 45 |
| Spanish Patent No. 2,050,069 | 63 | 85 | 54 |
| Present invention | performed simultaneously by one step | | no less than 80 |

As shown in Table 2, the method of the present invention is capable of providing risperidone in a markedly higher yield than any of the conventional methods.

While the invention has been described with respect to the above specific embodiments, it should be recognized that various modifications and changes may be made to the invention by those skilled in the art which also fall within the scope of the invention as defined by the appended claims.

What is claimed is:

1. A method of preparing risperidone of formula (I) which comprises reacting an oxime derivative of formula (II) with a haloethylpyrimidine derivative of formula (X) in a 20 to 40% (w/v) aqueous alkali hydroxide solution:

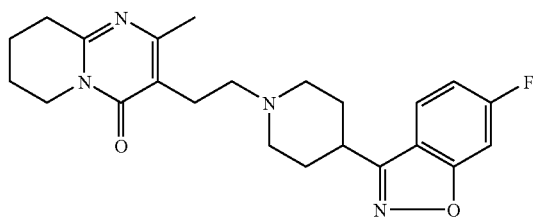
(I)

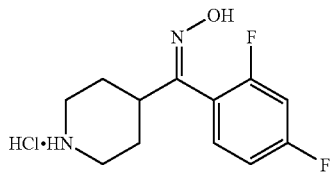
(II)

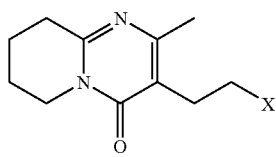
(X)

wherein, X is a halogen.

2. The method of claim 1, wherein the alkali hydroxide is selected from the group consisting of sodium hydroxide, potassium hydroxide, lithium hydroxide and a mixture thereof.

3. The method of claim 2, wherein the alkali hydroxide is potassium hydroxide.

4. The method of claim 1, wherein the aqueous alkali solution is employed in an amount ranging from 5 to 15 ml based on 1 g of the oxime derivative of formula (II).

5. The method of claim 1, wherein the haloethylpyrimidine derivative of formula (X) is employed in an amount ranging from 1.0 to 2.0 equivalents based on the amount of the oxime derivative of formula (II).

6. The method of claim 1, wherein the reaction is conducted at a temperature in the range of 100 to 140° C.

* * * * *